United States Patent [19]
Augst et al.

[11] Patent Number: 5,496,605
[45] Date of Patent: Mar. 5, 1996

[54] PERFORATED ROLL OF NONWOVEN SURGICAL TAPE

[75] Inventors: George W. Augst, Forest Lake; Margo A. Liberda, Stillwater, both of Minn.

[73] Assignee: Minnesota Mining and Manufacturing Company, St. Paul, Minn.

[21] Appl. No.: 516,691

[22] Filed: Aug. 18, 1995

Related U.S. Application Data

[63] Continuation of Ser. No. 114,912, Aug. 31, 1993, abandoned.

[51] Int. Cl.$^6$ ............................................. C09J 7/02
[52] U.S. Cl. ..................... 428/43; 206/447; 428/261; 428/343; 428/354
[58] Field of Search .......................... 428/43, 261, 343, 428/352, 354, 906; 206/447

[56] References Cited

U.S. PATENT DOCUMENTS

| Re. 24,906 | 12/1960 | Ulrich | 206/59 |
|---|---|---|---|
| 2,308,693 | 1/1943 | Goldman | 428/43 |
| 2,508,855 | 5/1950 | Brown | 428/43 |
| 2,870,840 | 1/1959 | Kwitek | 164/68 |
| 3,085,024 | 4/1963 | Blackford | 428/43 |
| 3,121,021 | 2/1964 | Copeland | 117/122 |
| 3,143,208 | 8/1964 | Sizemore | 428/43 |
| 3,331,728 | 7/1967 | Lane | 141/112 |
| 3,575,782 | 4/1971 | Hanson . | |
| 4,017,002 | 4/1977 | Doyle et al. | 221/63 |
| 4,292,360 | 9/1981 | Riedel et al. | 428/171 |
| 4,346,700 | 8/1982 | Dunshee et al. . | |
| 4,562,102 | 12/1985 | Rabuse et al. | 428/43 |
| 4,581,087 | 4/1986 | Johnson . | |
| 4,601,937 | 7/1986 | Latussek | 428/132 |
| 4,606,338 | 8/1986 | Greenway et al. | 128/156 |
| 4,671,266 | 6/1987 | Lengyel et al. | 128/156 |
| 4,704,113 | 11/1987 | Schoots | 604/379 |
| 4,737,393 | 4/1988 | Linkous | 428/43 |
| 4,768,810 | 9/1988 | Mertens | 282/12 |
| 4,772,499 | 9/1988 | Greenway | 428/43 |
| 4,882,213 | 11/1989 | Gaddis et al. | 428/136 |
| 4,908,251 | 3/1990 | Iimura et al. | 428/68 |
| 4,947,567 | 8/1990 | Hermann | 40/299 |
| 4,957,795 | 9/1990 | Riedel | 428/74 |
| 4,967,740 | 11/1990 | Reidel | 128/156 |
| 4,973,513 | 11/1990 | Reidel | 428/252 |
| 5,114,771 | 5/1992 | Ogg et al. | 428/43 |
| 5,198,276 | 3/1993 | Nakajima | 428/43 |
| 5,202,190 | 4/1993 | Kantner et al. | 428/447 |
| 5,213,565 | 5/1993 | Rollband | 602/41 |

FOREIGN PATENT DOCUMENTS

| 886474 | 1/1962 | United Kingdom . | |
| WO93/15245 | 8/1993 | WIPO | D04H 1/44 |

OTHER PUBLICATIONS

The B. F. Goodrich Company, Elastomers & Latex Division, "Elastoplast Latex" (2 pages).
Thwing–Albert Instrument Company, Instruction Manual for Handle–O–Meter, Model No. 211–30, Serial No. 46493, Jun. 1991, 14 pages.

*Primary Examiner*—Jenna L. Davis
*Attorney, Agent, or Firm*—Gary L. Griswold; Walter N. Kirn; Amy J. Hoffman

[57] ABSTRACT

A roll of linerless, perforated, nonwoven, surgical tape including a plurality of longitudinally spaced, laterally extending, perforated separation lines defined by a series of about 0.2 to 5 mm perforations separated by about 0.1 to 1 mm connecting segments of tape where the ratio of perforation length to connecting segment length in each separation line is about 1:1 to 10:1.

16 Claims, 2 Drawing Sheets

5,496,605

PERFORATED ROLL OF NONWOVEN SURGICAL TAPE

This is a continuing application of U.S. Ser. No. 08/114,912 filed on Aug. 31, 1993, abandoned.

FIELD OF THE INVENTION

The invention relates to nonwoven tapes. More specifically, the invention relates to rolls of linerless nonwoven surgical tape.

BACKGROUND

The random orientation of fibers in unoriented nonwoven fabrics provides such fabrics with a variety of useful properties and characteristics. One of these characteristics is the ability of such fabrics to resist continued linear tearing in the cross direction after introduction of an initial tear in the fabric. While this resistance-to-split characteristic of nonwoven fabrics is a beneficial attribute for various applications, it presents certain difficulties when nonwoven fabrics are used as the backing of adhesive tapes such as surgical tapes which are dispensed from a roll.

If the nonwoven backing is of sufficiently low strength, the tape can be torn by hand without much difficulty. U.S. Pat. No. 3,121,021 issued to Copeland and assigned to the Minnesota Mining & Manufacturing Company of St. Paul, Minn. describes such low-strength nonwoven adhesive medical tapes. The tapes disclosed by Copeland possess a tensile strength of about six pounds per inch width (1071 grams/cm). Although they can be torn by hand, these tapes tend to tear unevenly.

Tapes made with high-strength nonwoven backings, such as SONTARA™ fabrics are widely believed to be too tear resistant to be torn by hand and must be cut to size by scissors or other cutting tools. Nonwoven surgical tapes of this type are available in continuous roll form with a release liner laminated to the adhesive side of the tape. The liner serves to enhance the mechanical integrity of the web during the unwinding process and to facilitate cutting with scissors. The desired length of surgical tape is dispensed from the roll by unwinding the desired length and cutting through both the surgical tape and the liner with a pair of scissors. The liner is then peeled from the surgical tape to expose the adhesive and the tape applied to the patient. This method of dispensing is significantly more cumbersome than dispensing by hand-tearing from a linerless roll.

High-strength linerless nonwoven surgical tape has recently become available to health care professionals as precut pads with a nonadhesive separation tab positioned along one edge of each layer. Such pads of precut surgical tape are available from Minnesota Mining and Manufacturing Company of St. Paul, Minn. as MEDIPORE™ dressing covers. A single layer of surgical tape is dispensed from the pad by simply gripping the nonadhesive tab attached to the top layer of surgical tape and peeling the top layer from the pad. The surgical tape is then applied to the patient and the tab peeled away. MEDIPORE™ dressing covers have significantly improved the ease of dispensing surgical tape by eliminating the need for scissors and have reduced the amount of waste by significantly reducing the amount of release liner required.

However, despite the advances provided by MEDIPORE™ pre-cut dressing covers, a need still existed for a completely linerless and tabless nonwoven surgical tape in roll form which could be dispensed without the need for scissors or other cutting tools and which tears cleanly and evenly.

One approach to providing a tearable nonwoven web is disclosed in Greenway, U.S. Pat. No. 4,772,499. Greenway suggests applying binder to the nonwoven web in spaced linear bands so that the web can be torn in a linear fashion along the binder-free bands of web. Unfortunately, the cost of producing such a banded nonwoven web is prohibitive for many purposes and differences in the surface characteristics of the web as between the binder-free and binder-containing bands would significantly complicate manufacture of the web and it is perceived that it would detract from the performance of the tape.

Patent Cooperation Treaty Publication WO 93/15245 filed by the Minnesota Mining and Manufacturing Company of St. Paul, Minn. discloses an embossed nonwoven tape including both staple and binder fibers. The specific composition of the tape in combination with the embossed pattern on the tape renders the tape tearable in the cross-machine direction along an embossed pattern in the tape. The tearable tapes disclosed by this publication are limited to those which include a significant proportion of melt-activated binder fibers.

SUMMARY OF THE INVENTION

According to the present invention, there is provided linerless binder-containing nonwoven tape which is capable of being dispensed without the need for cutting tools. The roll of tape includes a plurality of longitudinally spaced, laterally extending, perforated separation lines defined by a series of about 0.2 to 5 mm perforations separated by about 0.1 to 1 mm connecting segments of tape where the ratio of perforation length to connecting segment length in each separation line is about 1:1 to 10:1.

DETAILED DESCRIPTION OF THE INVENTION

Definitions

As used herein, including the claims, the term "surgical tape" means a web of woven or nonwoven fabric which is coated on a major surface with a skin-compatible pressure sensitive adhesive.

As used herein, including the claims, "perforation length" is measured as the distance between longitudinal lines passing through the lateral extremities of the two connecting segments bounding the perforation.

As used herein, including the claims, "connecting segment length" means the shortest distance between adjacent perforations.

Nomenclature

Figure 5:
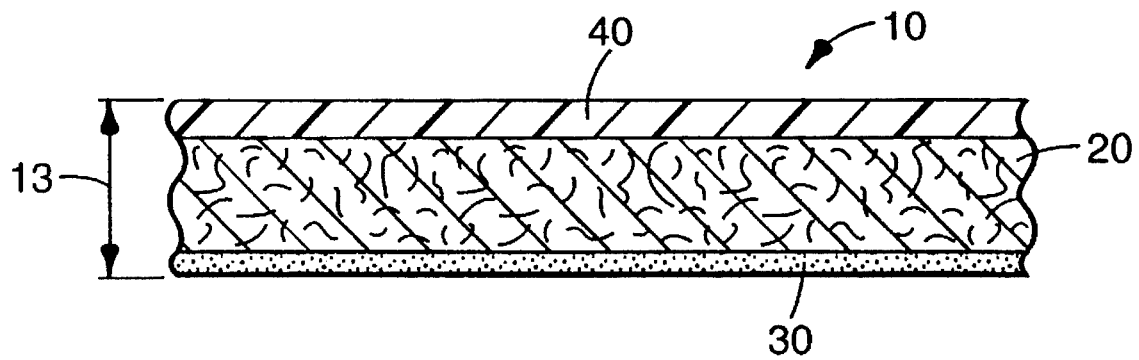
FIG. 5 is an enlarged cross-sectional side view of the tape of Figure 1 taken along line 5—5.

10 Tape
11 Longitudinal Direction of Tape
12 Lateral Direction of Tape 13 Thickness of Tape
20 Nonwoven Web
30 Pressure Sensitive Adhesive
40 Low Adhesion Backsize
50 Separation Line
60 Perforations
60d Length of Perforations
70 Connecting Segments
70d Length of Connecting Segments
80 Individual Sheets of Tape
100 Core Composition As seen most clearly in FIG. 5, the tape 10 of the invention is a binder-containing nonwoven web 20 which is coated on a first major surface with a pressure sensitive adhesive 30 and on a second major surface with a low adhesion backsize 40.

Figure 1:
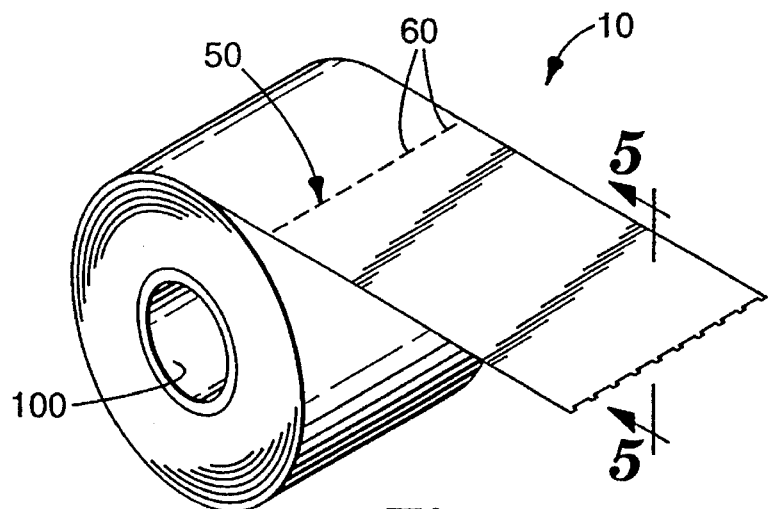
FIG. 1 is a perspective view of one embodiment of a roll of tape manufactured in accordance with the present invention.
Figure 2:
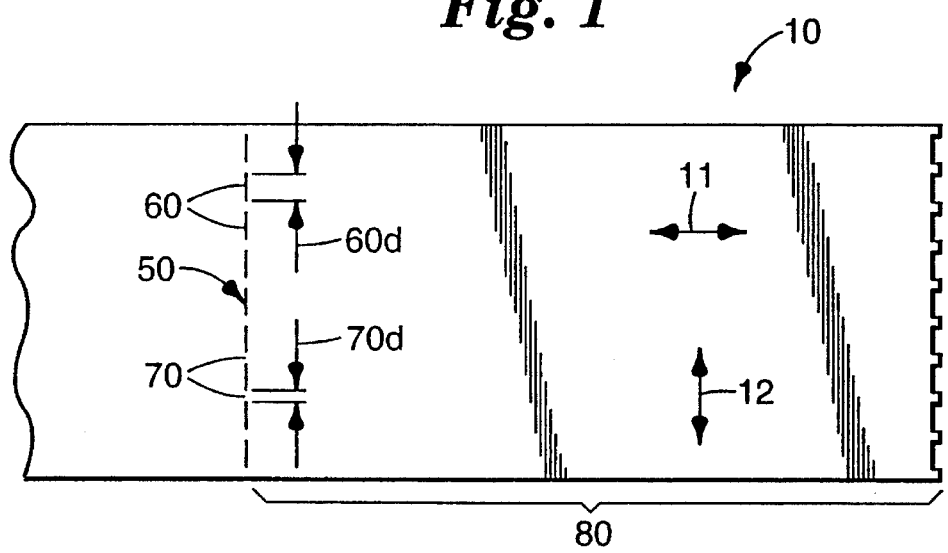
FIG. 2 is a top view of the tape of FIG. 1.
Figure 3:
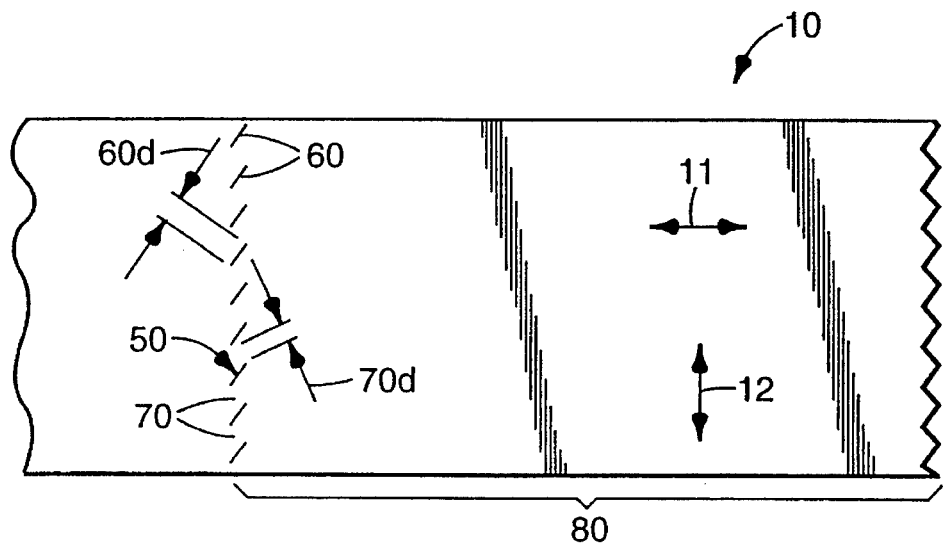
FIG. 3 is a top view of a first alternative embodiment for the separation line in the tape of the present invention.
Figure 4:
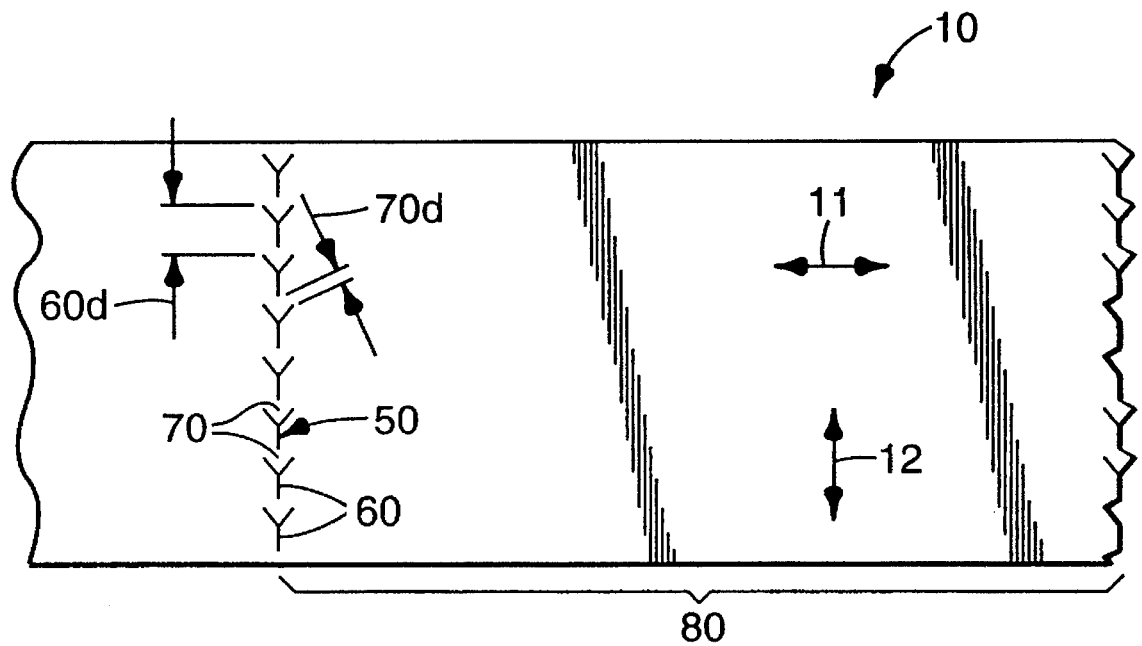
FIG. 4 is a top view of a second alternative embodiment for the separation line in the tape of the present invention.

Tape 10 is rolled onto core 100 (FIG. 1) or a strip of consecutive sheets 80 of the desired length. To facilitate dispensing individual sheets of tape 80 from the roll, perforated separation lines 30 extending laterally across the tape are uniformly spaced longitudinally along the length of the roll. As seen in FIGS. 2 and 3, each separation line 30 is defined by a series of perforations 60, each of which has a perforation length 60D between about 0.2 and 5 mm. The connecting segments 70 between the perforations 60 are between about 0.1 and 1 mm in length (70D). The ratio of the perforation length 60D to the connecting segment length 70D is about 1:1 to 10:1.

Nonwoven Web

The nonwoven web 20 may be manufactured by any of the well known methods for manufacturing nonwovens including melt-blowing, spin-bonding, carding, aerodynamic entanglement, etc. A particularly preferred method for making a nonwoven web 20 useful in the practice of this invention is by a technique known as hydroentangling. This process is described in U.S. Pat. Nos. 3,485,706, 3,486,168, 3,493,462, 3,494,821 and 3,508,308. Briefly, fibers are supported on a perforated plate or similar support screen and traversed with high energy liquid streams so as to consolidate the material in a repeating pattern of entangled fiber regions and interconnecting fibers. An alternate method of forming a nonwoven web 20 is needle-tacking as described in U.S. Pat. No. 5,016,331.

The thickness of the nonwoven web 20 is largely dependant upon the intended use of the tape 10. Generally, a thickness of about 0.2 to about 0.6 mm is suitable for most intended uses. For use as a surgical tape 10, a thickness of about 0.1 to about 0.4 mm is typically desired.

The weight of the nonwoven web 20 is preferably from about 10 g/m$^2$ to about 100 g/m$^2$, more preferably from about 15 g/m$^2$ to about 70 g/m$^2$, and most preferably from about 20 g/m$^2$ to about 50 g/m$^2$.

Preferred nonwoven webs 20 include a family of high-strength nonwoven fabrics available from E.I. Dupont de Nemuours & Company of Wilmington, Del. under the trademark SONTARA™ including SONTARA™ 8010, a hydroentangled polyester fabric. Other suitable nonwoven webs 20 include a hydroentangled polyester fabric available from Veratec, a division of International Paper of Walpole, Mass. This fabric is preferably bonded with HYSTRETCH™ V-43 binder, an elastomeric terpolymer available from the BF Goodrich Company.

The nonwoven web 20 must include one of the well known binders for enhancing bonding of the individual fibers within the web 20. Selection of a suitable binder (i.e., one which has a suitable affinity for the fibers of the nonwoven web 20) is well within the judgment of one skilled in the art. Briefly, binders for nonwoven fabrics are typically selected from such materials as homopolymer and copolymer latexes of acrylics, butadienes, styrene/butadiene rubber copolymers, urethanes, vinyl acetates, vinyl acetate/ acrylate copolymers, vinyl acetate/ethylene copolymers, polyvinyl alcohols, polyvinyl chlorides, vinyl esters, vinyl ethers, etc.

Specific examples of latex binding agents include, RHOPLEX™ E-2559 (an approximately 45% solids acrylic latex binder) available from the Rohm & Hass Co. of Philadelphia, Pa.; UNICAL™ 76-4402 (an approximately 50% solids styrene/butadiene rubber latex) available from the UNICAL Corp. of Charlotte, N.C.; NATIONAL STARCH™ No. 78-6283 (an approximately 45% solids acrylic/vinyl acetate copolymer latex) available from the National Starch Corp. of Bridgewater, N.J.; and the KRATON™ family of thermoplastic rubbers available from the Shell Oil Company of Oak Brook, Ill.

Additional binders include the various thermoplastic fibers which may be incorporated directly in the nonwoven web. The nonwoven web 20 is bonded by simply incorporating about 5 to 10 wt % of a compatible thermoplastic fiber into the nonwoven web 20 and heating the web 20 above the softening temperature of the thermoplastic fibers so as to bond the thermoplastic fibers to the staple fibers in the web 20. A compatible thermoplastic fiber is a fiber capable of melt-bonding to the other fibers in the web 20 without substantially weakening the web 20.

Binder fibers are available in a wide variety of configurations including totally meltable binder fibers, side-by-side binder fibers, bicomponent binder fibers, elliptical core-sheath binder fibers, concentric core-sheath binder fibers, and combinations thereof.

Examples of suitable binder fibers include, binder fibers of polyester, polyethylene, polypropylene, polybutylene, polyamide and combinations thereof. The binder fibers are preferably from about 1 cm to about 20 cm in length and display a fineness of from about 0.1 denier to about 20 denier.

Specific examples of suitable core-sheath binder fibers for use in the nonwoven web 20 include, DIAWA™ binder fibers (1½ denier by 38 mm crystalline polypropylene core with meltable polyethylene sheath) and MELTY™ binder fibers (2 denier by 38 mm oriented polyester core with meltable polyester sheath) available from Chori America, Inc. of Los Angeles, Calif.; and K-52™ binder fibers (2 denier by 38 mm oriented polyester core with meltable polyester sheath) and K-54™ binder fibers (2 denier by 38 mm oriented polyester core with meltable polyester sheath) available from Hoechst Celanese Corp. of Charlotte, N.C.

The enhanced fiber bonding achieved with binders tends to stiffen the web 20 and thereby facilitate tearing of the web 20, improve handleability of the tape 10 during application, and control fraying of the fibers along the tear line. However, as understood by those skilled in the art, when intended for use as surgical tape 10, the amount of binder employed must be controlled so as to provide the surgical tape 10 with a softness and conformability acceptable to both health care professionals and patients. The surgical tape 10 should posses sufficient stiffness to facilitate application of the tape 10 while retaining sufficient conformability to be comfortable to the patient and maintain contact with the skin over prolonged periods of use.

Both high-strength and low-strength tapes 10 can benefit by incorporating the separation lines 50 described herein. High-strength tapes 10, i.e., those with a tensile strength of greater than about 10 lbs/inch (about 1800 g/cm) are difficult to tear and do not generally tear in a linear fashion. Low-strength tapes, i.e., those with a tensile strength of less than about 10 lbs/inch (about 1800 g/cm) are tearable but do not generally tear evenly and may wrinkle during tearing to such an extent that the tape 10 can become adhesively adhered to itself. The perforation of tapes 10 in accordance with this invention is particularly beneficial when the tape 10 (including the nonwoven web 20, binder, low adhesion backsize 40 and adhesive 30) is a high-strength tape 10 having a tensile strength prior to perforation of greater than about 10 lbs/inch (about 1800 g/cm).

Adhesive

The adhesive 30 is a pressure sensitive adhesive 30 which, in the case of surgical tapes, is physically and biologically compatible with human skin. A wide variety of suitable, skin-compatible, pressure sensitive adhesives 30 are known to those skilled in the art and include specifically, but not exclusively, acrylic-based adhesives, polyolefin adhesives, rubber-based adhesives, tackified styrene block copolymer adhesives, and the like.

A preferred pressure sensitive adhesive 30 is any of the copolymers of isooctyl acrylate and acrylic acid or acrylamide described in U.S. Pat. No. Re. 24,906 issued to Ulrich. Such adhesives are preferred for use on surgical tapes since they are relatively nonirritating to the skin.

Low Adhesion Backsize

A layer of low adhesion backsize 40 is preferably applied to the nonwoven web 20. Application of low adhesion backsize 40 to the nonwoven web 2O provides a surface with a reduced adhesive affinity for the pressure sensitive adhesive 30. Such reduced adhesion facilitates the unwinding of tape 10 from a linerless roll of the tape 10.

Materials suitable for use as a low adhesion backsize 40 in this invention, include acrylates, fluorochemicals, polyethylenes, silicones, vinyl copolymers and combinations of these compounds. Compounds suitable as a low adhesion backsize 40 are disclosed in U.S. Pat. No. 4,728,571 issued to Clemens et al. A specific example of a suitable low adhesion backsize 40 is SYL-OFF™, a silicone compound available from Dow Corning Corp. Preferred low adhesion backsize 40 are the siloxane and acrylate based compounds disclosed in U.S. Pat. No. 4,973,513 issued to Riedel and the water-insoluble hydrophobic urethane (carbamate) copolymer of polyvinyl alcohol and octadecyl isocyanate disclosed in U.S. Pat. No. 2,532,011 issued to Dahlquist et al.

Separation Lines

The relative lengths 60d and 70d of perforations 60 and connecting segments 70 control several fundamental properties of tape 10 related to dispensibility and performance. For example, length 70d of the connecting segments 70 is one factor controlling the tensile strength between individual sheets 80 of tape 10. Separation of sheets 80 becomes difficult when the connecting segments 70 are too long while accidental and unintended separation is likely when the connecting segments 70 are too short.

The physical dimensions of the perforations 60 and connecting segments 70 defining the separation lines 50 are important aspects of the invention. An acceptable balance must be achieved between the competing interests of adequate tensile strength to prevent premature separation and sufficient reduction in tensile strength to ensure easy and consistent separation of sheets 80 along a single separation line 50.

The parameters of separation lines 50 necessary to define performance are perforation length 60d, connecting segment length 70d and the ratio of perforation length 60d to connecting segment length 70d. Acceptable values for achieving proper performance of the perforated tape 10 of this invention are set forth below in Table One. The interdependence of these variables and the cooperational manner in which they effect and influence performance of the tape 10 requires that they be considered together.

TABLE ONE

| Variable | Acceptable | Preferred | Highest Performance |
|---|---|---|---|
| Perforation Length (mm) | 0.2–5.0 | 0.5–3.0 | 1.0–2.0 |
| Connecting Segment Length (mm) | 0.1–1.0 | 0.2–0.8 | 0.3–0.6 |
| Ratio Perforation Length -to- Connecting Segment Length | 1:1 to 10:1 | 2:1 to 8:1 | 3:1 to 6:1 |

The tensile strength of the perforated section of tape 10 in the longitudinal direction 11 (FIG. 2) measured in accordance with the protocol set forth herein, is desirably from about 400 to about 3000 grams/cm width, preferably from about 600 to about 2000 grams/cm width, and most preferably from about 800 to about 1700 grams/cm width. A longitudinal tensile of less than about 400 grams/cm width tends to result in premature separation of the sheets 80 while a longitudinal tensile of greater than about 3000 grams/cm width tends to require excessive force and thereby hinder separation of the sheets 80.

A secondary consideration is the shape of the perforations 60 and connecting segments 70. Shape is designated a secondary consideration because, while relevant to dispensibility and performance of the tape 10, its impact is not as critical as the primary considerations of perforation length 60d, connecting segment length 70d and ratio of perforation length 60d to connecting segment length 70d. The perforations 60 may be shaped in accordance with any of the accepted perforation patterns including linear, angled, Y-shaped, V-shaped, dual-angled offset, sinusoidal, etc. When angled, the perforations 60 are preferably angled about 30° to 60° from the lateral axis 12 of the tape 10. The preferred shape, based upon ease of manufacture and minimization of fraying along the torn edge, is a simple linear pattern extending laterally across the tape 10 as shown in FIG. 2.

Similarly, the longitudinal distance between the separation lines 50 must be selected so as to balance the competing interests of permitting substantially any length of tape 10 to be created (more separation lines 50) and limiting the accidental and unintended separation of the tape 10 along a separation line 50 during dispensing, application or use (fewer separation lines 50). Generally, a longitudinal spacing of about 1 to about 20 cm, preferably about 2 to about 10 cm provides an acceptable balance between these competing interests.

Method of Manufacture

Application of Binder

The binder may be applied after formation of the nonwoven web 20 by any of the conventional water or solvent-based coating techniques including air knife, trailing blade, direct and offset gravure, Meyer bar, wire-wound rod, reverse roll, roll coating, print bond and spray coating. Where the binder is a thermoplastic fiber, the fiber is simply dispersed into the fiber matrix prior to formation of the web 20 and then melted.

Application of Low Adhesion Backsize

Similarly, the low adhesion backsize 40 may be applied by any of the conventional coating techniques discussed in connection with the application of a binder.

A dried coating weight of about 0.1 to about 0.4 $mg/cm^2$ is preferred for the low adhesion backsize and about 0.2 to 0.8 $mg/cm^2$ for the binder.

The binder and the low adhesion backsize 40 may optionally be mixed together and simultaneously coated onto the nonwoven web 20 in accordance with the procedure outlined in the Examples section of this disclosure and disclosed in U.S. Pat. No. 4,967,740 issued to Riedel and assigned to Minnesota Mining & Manufacturing Company of St. Paul, Minn.

Application of Adhesive

The pressure sensitive adhesive 30 may be applied to the nonwoven web 20 by any of the well known techniques for coating pressure sensitive adhesives such as dispersion coating, solution coating and hot melt application. A convenient method of coating the nonwoven web 20 with the pressure sensitive adhesive 30 is disclosed in U.S. Pat. No. 3,121,021 issued to Copeland. Briefly, a pressure sensitive adhesive 30 is coated on a smooth release liner. The release liner carrying the adhesive film is then laminated to the nonwoven web 20, the release liner peeled away, and the linerless tape 10 wound into a "jumbo" roll.

Alternatively, the adhesive 30 may be applied by such conventional coating techniques as air knife, trailing blade, direct and offset gravure, wire-wound rod, reverse roll, print bond, spray coating, etc.

Perforating

The separation lines 50 are conveniently created with a rotary die having a serrated perforator blade(s) positioned along the periphery of the die so as to perforate the tape 10 at the desired intervals. Other perforation methods known in the art, e.g., laser perforation, may also be used.

The separation lines 50 will generally be invisible to the user during both dispensing and use. Dependent upon consumer preference, the separation lines 50 may optionally be marked, such as with a compatible pigment at the point of perforation, or otherwise distinguished, so that the user dispensing the tape 10 can see the separation lines 50.

Converting

The "jumbo" rolls of tape 10 are converted into multiple rolls of commercially sized tape 10 by conventional converting techniques including unwinding, longitudinally slitting, rewinding, and laterally cutting.

Method of Use

The tape 10 is dispensed by simply gripping the free end of the tape, unrolling the desired length, and then tearing the tape along a separation line 50. When separating the desired length of tape from the roll, it is generally desired to grip the sheet 80 of tape 10 closest to the roll to prevent other separation lines 50 from tearing.

Utility of the tape disclosed and claimed herein is not limited to uses involving contact to human skin.

EXPERIMENTAL

Protocols

Tensile Strength,

% Elongation

Thwing-Albert

Testing is conducted upon a THWING-ALBERT INTELECT™ II (Model No. 1450-42-C) constant rate of extension tensile tester equipped with clamp-type jaws manufactured by the Thwing-Albert Instrument Company of Philadelphia, Pa.

Rectangular test samples of 1"×9" are cut from a roll of the tape to be tested. The long dimension is cut in the direction (machine or cross-machine) to be tested. The ends of the test samples are folded adhesive-to-adhesive to form a two inch nonadhesive tab at each end. The nonadhesive tabs prevent the sample from being pulled out of the jaws, reduces premature jaw breaks, and prevents the sample from leaving an adhesive residue on the jaws. The samples are positioned within the jaws of the Thwing-Albert tester and the tester set at a crosshead speed of 5 inches per minute, a chart speed of 10 inches per minute and a gauge length of 5 inches. The chart recorder is set at 0.1 inch per chart division in the cross direction and 0.2 inch per chart division in the machine direction. The machine is activated and the sample pulled apart until the force required to pull the sample decreases.

Tensile strength is calculated in accordance with the equation set forth below where "Pen Height$_{max}$" is the number of small divisions in the cross direction reached by the pen in its maximum travel across the chart.

$$\text{Tensile Strength} = (\text{Load Range})(\text{Pen Height}_{max})/(100)$$

Elongation is calculated in accordance with the equation set forth below where "Pen Distance$_{max}$" is the number of small divisions reached by the pen in the machine direction from initiation of pen deflection to sample break.

$$\% \text{ Elongation} = \frac{(20)(\text{Pen Distance}_{max})(\text{Crosshead Speed})}{(\text{Gauge Length})(\text{Chart Speed})}$$

Tear Strength

Falling Pendulum Elmendorf Apparatus

Testing is conducted upon a THWING-ALBERT Model #60 ELMENDORF type falling pendulum tear tester. The samples to be tested are conditioned in accordance with ASTM D 1776 and tested according to ASTM D 1424.

Test samples are cut with a 63×100 mm (2.5"×4") cutting die. The samples are clamped into position in the ELMENDORF apparatus and a 20 mm long linear slit cut into the side of the sample fabric leaving a 43 mm long testing width. The capacity of the ELMENDORF apparatus is selected to effect a desired tear in the sample at a loading of between 20% and 60% of the scale value.

The test is conducted on a set of five samples cut in the machine direction (long dimension parallel to the machine direction). The results are averaged. Test values are discarded when the sample slips from the jaws or the tear deviates more than 6 mm (0.24 inches) from the projection of the original slit.

Tear Strength (Tear$_{CD}$) is calculated by multiplying the average test value by the appropriate factor found in ASTM 1424; ANNEX A 1.4; Table A1.

Test Samples

A fabric backing of SONTARA™ 8010 was laminated with light pressure to a coating of pressure sensitive adhesive containing 90–96 wt % solids. This adhesive was coated on the surface of a silicone release-coated carrier. The pressure sensitive adhesive was a copolymer of 97/3 weight ratio of iso-octyl acrylate and acrylamide. An adhesive of this type is described in U.S. Pat. No. RE. 24,906, Example 6.

The carrier/adhesive backing laminate was dipped at a constant feed rate into a trough containing one part low adhesion backsize and one part of binder.

The low adhesion backsize used was a 5% solution of polyvinyl N-octadecyl carbamate in toluene and xylene— ratio 90/10 by weight. This type of low adhesion backsize is described in column 9 of U.S. Pat. No. 2,532,011.

The binder used was a 10% by weight solution of KRATON™ 1101, a thermoplastic rubber obtained from Shell Oil Company of Oak Brook, Ill., in toluene.

Additional description of the formulation and coating of combined low adhesion backsize and binder is found in U.S. Pat. No. 4,967,740.

Following the binder/low adhesion backsize coating step, the wet tape construction passed through a two-stage drying oven. The first stage was at 100° C. for about 30 seconds and the second stage was at 135° C. for about 2.5 minutes.

The dried tape was removed from the silicone release coated carrier and was wound onto a spool to form a "jumbo" roll of adhesive tape.

The tape was then laterally perforated with a rotary die to form separation lines with linear perforations. The separation lines were two inches apart and had perforation lengths, connecting segment lengths, and a ratio of perforation to connecting segment lengths as specified in Table Two. The perforated tape was then tested for Average Cross Direction Tear Strength ($Tear_{CD}$), Average Machine Direction Tensile Strength ($T_{MD}$) and Average Machine Direction Elongation ($E_{MD}$) with the results set forth in Table Two.

Hand Tear Test

Perforated tape sample rolls of various perforation patterns were evaluated by a panel of eight people. Evaluation criteria included ease of tear, appearance of torn area, and perceived tape tensile strength. Acceptable and preferred performance were noted for samples #4, 7, 9, and 10 as indicated in Table 2.

3. The roll of tape of claim 1 wherein the nonwoven web is hydroentangled.

4. The roll of tape of claim 1 wherein the nonwoven web is comprised of polyester fibers.

5. The roll of tape of claim 1 wherein the perforated separation lines are uniformly longitudinally spaced about 1 to 20 cm apart to define individually separable sheets of tape having identical longitudinal lengths.

6. The roll of tape of claim 1 wherein the perforated separation lines are uniformly longitudinally spaced about 2 to 10 cm apart to define individually separable sheets of tape having identical longitudinal lengths.

7. The roll of tape of claim 1 wherein the perforated separation lines are defined by perforations which are about 0.5 to 3 mm long, connecting segments which are about 0.2 to 0.8 mm long, and a ratio of perforation length to connecting segment length of about 2:1 to 8:1.

8. The roll of tape of claim 1 wherein the perforated separation lines are defined by perforations which are about 1 to 2 mm long, connecting segments which are about 0.3 to 0.6 mm long, and a ratio of perforation length to connecting segment length of about 3:1 to 6:1.

9. The roll of tape of claim 1 wherein the perforations are linear perforations which extend laterally across the tape.

10. The roll of tape of claim 1 wherein the perforations are linear perforations which extend at an angle of about 30° to 60° from the lateral axis of the tape.

11. The roll of tape of claim 1 wherein the perforations are nonlinear perforations.

TABLE TWO

| | Separation Lines | | | | Perforated Tape Test Results | |
| --- | --- | --- | --- | --- | --- | --- |
| | | | | | Tear Force | Tensile; |
| Sample # | Cut Length in CM. | Uncut Length in CM. | Cut to Uncut Ratio | Hand Tear Test | $Tear_{CD}$ (in grams) | $T_{MD}$ (in GMS/CM) |
| 1 | 0.54 | 0.25 | 2.1:1 | | 691.4 | 2824 |
| 2 | 0.39 | 0.41 | 0.95:1 | | 1394.9 | 3056 |
| 3 | 0.94 | 0.25 | 3.8:1 | | 847.9 | 1198 |
| 4 | 0.78 | 0.41 | 1.9:1 | Acceptable | 418.8 | 1698 |
| 5 | 0.68 | 0.51 | 1.3:1 | | 838.5 | 2306 |
| 6 | 1.33 | 0.25 | 5.3:1 | | 297.6 | 840 |
| 7 | 1.18 | 0.41 | 2.9:1 | Acceptable | 521.2 | 1162 |
| 8 | 1.08 | 0.51 | 2.1:1 | | 694.1 | 2627 |
| 9 | 1.58 | 0.41 | 3.9:1 | Preferred | 393.9 | 1001 |
| 10 | 1.48 | 0.51 | 2.9:1 | Acceptable | 492.8 | 1573 |
| Control (Unperfed) | — | — | — | | 1775.9 | 3485 |

We claim:

1. A roll of adhesive tape comprising a binder-containing nonwoven web having a longitudinal axis and a lateral axis which is coated on a major surface with a pressure sensitive adhesive which web is substantially resistant to tearing along the lateral axis and which is linerless; the adhesively-coated web having a plurality of longitudinally spaced, laterally extending, perforated separation lines defined by a series of about 0.2 to 5 mm substantially linear perforations separated by about 0.1 to 1 mm connecting segments of tape and a ratio of perforation length to connecting segment length of about 1:1 to 10:1 wherein the perforated tape has a tensile strength of at least about 400 grams per centimeter width and not more than about 3000 grams per centimeter width.

2. The roll of tape of claim 1 further comprising a low adhesion backsize.

12. The roll of tape of claim 1 wherein the perforations in each separation line have a uniform length.

13. The roll of tape of claim 9 wherein the perforations in each separation line have a uniform shape.

14. A roll of surgical tape comprising:

(a) a core, and (b) a length of linerless adhesive tape wound around the core;

(c) wherein the tape comprises at least (i) a binder-containing nonwoven fabric coated on a major surface with a skin compatible pressure sensitive adhesive which is substantially resistant to tearing across the width of the tape, and (ii) a plurality of longitudinally spaced, laterally extending, perforated separation lines defined by a plurality of about 0.2 to 5 mm substantially linear perforations separated by about 0.1 to 1 mm connecting segments of tape and a ratio of perforation length to connecting segment length of about 1:1 to 10:1 wherein the perforated tape has a tensile strength of at least about 400 grams per centimeter width and not more than about 3000 grams per centimeter width.

15. A method of dispensing nonwoven tape comprising the steps of:

(a) unwinding a length of linerless tape from a wound core of the tape wherein the tape comprises a binder-containing nonwoven web coated on a major surface with a pressure sensitive adhesive which tape is substantially resistant to tearing across the width of the tape which includes a plurality of longitudinally spaced, laterally extending, perforated separation lines defined by a plurality of longitudinally spaced, defined by a plurality of about 0.2 to 5 mm substantially linear perforations separated by about 0.1 to 1 mm connecting segments of tape and a ratio of perforation length to connecting segment length of about 1:1 to 10:1 wherein the perforated tape has a tensile strength of at least about 400 grams per centimeter width and not more than 3000 grams per centimeter width, and (b) laterally tearing the tape along a separation line to detach a length of tape from the tape remaining on the core.

16. A roll of adhesive tape comprising a binder-containing nonwoven fabric having a longitudinal axis and a lateral axis which is linerless, coated on a major surface with a pressure sensitive adhesive, and is substantially resistant to tearing along the lateral axis; the adhesively-coated web having a plurality of longitudinally, about uniformly spaced, laterally extending, perforated separation lines defined by a series of about 0.2 to 5 mm substantially linear perforations separated by about 0.1 to 1 mm connecting segments of tape and a ratio of perforation length to connecting segment length of about 1:1 to 10:1; wherein the perforated tape has a tensile strength of at least 400 grams per centimeter width and not more than 3000 grams per centimeter width.

* * * * *